(12) United States Patent
Ramji et al.

(10) Patent No.: US 8,007,771 B2
(45) Date of Patent: Aug. 30, 2011

(54) FLAVORS FOR ORAL COMPOSITIONS

(75) Inventors: Niranjan Ramji, Mason, OH (US); Marc Hester, Cincinnati, OH (US); Steve Hoke, West Chester, OH (US); Robert Leslie Swaine, Jr., Glendale, OH (US); Gerhard Norbert Zehentbauer, Okeana, OH (US)

(73) Assignee: The Procter & Gamble Company, Cincinnati, OH (US)

(*) Notice: Subject to any disclaimer, the term of this patent is extended or adjusted under 35 U.S.C. 154(b) by 0 days.

(21) Appl. No.: 11/825,177

(22) Filed: Jul. 5, 2007

(65) Prior Publication Data

US 2008/0008665 A1 Jan. 10, 2008

Related U.S. Application Data

(60) Provisional application No. 60/819,154, filed on Jul. 7, 2006, provisional application No. 60/819,156, filed on Jul. 7, 2006.

(51) Int. Cl.
*A61K 8/00* (2006.01)
*A61K 8/19* (2006.01)
*A61K 8/20* (2006.01)
*A61K 8/21* (2006.01)
*A61K 31/11* (2006.01)
*A61K 31/30* (2006.01)
*A61K 31/32* (2006.01)
*A61Q 11/00* (2006.01)

(52) U.S. Cl. ............ 424/49; 424/52; 424/401; 514/493; 514/499; 514/693; 514/699; 514/703

(58) Field of Classification Search .................... 424/49, 424/52, 401; 514/493, 499, 693, 699, 703
See application file for complete search history.

(56) References Cited

U.S. PATENT DOCUMENTS

| | | | |
|---|---|---|---|
| 3,105,013 | A | 9/1963 | Everett |
| 3,867,262 | A | 2/1975 | Rockland et al. |
| 4,112,066 | A | 9/1978 | Hussein |
| 4,335,102 | A | 6/1982 | Nakashima et al. |
| 4,440,790 | A | 4/1984 | Blackwell et al. |
| 4,476,142 | A | 10/1984 | Netherwood et al. |
| 4,613,513 | A | 9/1986 | Hussein |
| 4,708,880 | A | 11/1987 | Hussein |
| 4,778,691 | A | 10/1988 | Todd et al. |
| 4,861,616 | A | 8/1989 | Spencer |
| 4,948,595 | A | 8/1990 | Patel et al. |
| 5,030,459 | A | 7/1991 | Barcelon et al. |
| 5,047,251 | A | 9/1991 | Spencer |
| 5,116,625 | A | 5/1992 | Patel et al. |
| 5,128,154 | A | 7/1992 | Johnson |
| 5,204,128 | A | 4/1993 | Johnson |
| 5,298,238 | A | 3/1994 | Hussein et al. |
| 5,372,824 | A | 12/1994 | Record et al. |
| 5,425,962 | A | 6/1995 | Johnson et al. |
| 5,582,694 | A | 12/1996 | McClelland et al. |
| 6,042,812 | A * | 3/2000 | Sanker et al. ................... 424/49 |
| 6,365,215 | B1 * | 4/2002 | Grainger et al. .............. 426/535 |
| 6,479,088 | B1 | 11/2002 | Johnson |
| 2003/0152527 | A1 * | 8/2003 | Glandorf et al. ................ 424/52 |
| 2006/0153958 | A1 * | 7/2006 | Behan et al. ................... 426/534 |
| 2008/0008667 | A1 | 1/2008 | Hoke |
| 2008/0008729 | A1 | 1/2008 | Swaine, Jr. |

FOREIGN PATENT DOCUMENTS

| | | |
|---|---|---|
| EP | 0321180 | 6/1989 |
| EP | 0349186 A2 | 1/1990 |
| EP | 0425002 | 5/1991 |
| WO | WO9427566 A1 | 12/1994 |
| WO | WO9600014 A1 | 1/1996 |

OTHER PUBLICATIONS

Takahahi et al., A New Keto-alcohol, (−)-Minolactone, (+)-isoMintlactone and Minor components in Peppermint Oil, Agric. Biol. Chem., 44(7),pp. 1535-1543, 1980.*

Scott Benn, Potent Odorants in Peppermint an Cornmint Oils Characterized by GC-O and AEDA, *Perfumer & Flavorist*, vol. 23, Sep./Oct. 1998, pp. 5-16, International Mint Symposium, Seattle, Washington, in 1997.

William Coleman, III, et al, "The Uses of a non-equilibrated solid phase microextraction method to quantitatively determine the off-notes in mint and other essential oils", *Journal of Science of Food and Agriculture*, 2004, pp. 1223-1228, vol. 84, Issue 10.

William Coleman, III, et al, "Semiquantitative Determination of Off-Notes in Mint Oils by Solid Phase Microextraction", *Journal of Chromatographic Science*, vol. 40, Mar. 2002.

David Moyler, et al, Mint Oils: Potential for Standardizing Profiles with Natural Flavoring Substances, *Perfumer & Flavorist*, vol. 23, pp. 37-42, vol. 23, Mar./Apr. 1998, Allured Publishing Corp.

Levy Canova, "The Composition of Scotch Spearmint Oil", Anais da Academia Brasileira de Ciencia, vol. 44(7): pp. 273-277, 1972, V Congresso Internacional De Oleos Essenciais, Rio De Janeiro.

D.R. Dhingra, et al, Peppermint Oil and the Possibility of Its Production in Uttar Pradesh, *Indian Soap Journal*, vol. 17, pp. 43-51, Aug. 1951, H.B. Technological Institute, Kanpur.

O.Johnson and J.C. Snyder, "Peppermint Oil Production in Washington", *Bulletin* 1936, pp. 3-8.

(Continued)

*Primary Examiner* — James H. Alstrum-Acevedo
(74) *Attorney, Agent, or Firm* — Emelyn L. Hiland

(57) ABSTRACT

The present invention relates to oral care compositions comprising stannous ions, a mint-type flavor oil, a protectant component that prevents generation of off odor and off taste in the composition, and orally acceptable carriers. The mint-type oils include peppermint, spearmint and corn mint. Suitable protectant components include copper salts and carbonyl compounds such as ascorbic acid; cis-jasmone; 2,5-dimethyl-4-hydroxy-3(2H)-furanone; 5-ethyl-3-hydroxy-4-methyl-2(5H)-furanone; vanillin; ethyl vanillin; anisaldehyde; 3,4-methylenedioxybenzaldehyde; 3,4-dimethoxybenzaldehyde; 4-hydroxybenzaldehyde; 2-methyoxybenzaldehyde; 4-methoxybenzaldehyde; benzaldehyde; cinnamaldehyde (3-phenyl-2-propenal); hexyl cinnamaldehyde; α-methyl cinnamaldehyde; ortho-methoxy cinnamaldehyde; α-amyl cinnamaldehyde; and combinations thereof. The oral care composition may be a dentifrice.

7 Claims, No Drawings

OTHER PUBLICATIONS

Katsuhiro Takahashi, et al, A New Keto-alcohol, (−) Mintlactone, (+)-*iso*Mintlactone and Minor Components in Peppermint Oil, Agric. Biol. Chem., 44(7), pp. 1535-1543, 1980, Dec. 19, 1979.

Thomas W. Pearson, et al, "Natural Occurring Levels of Dimethyl Sulfoxide in Selected Fruits, Vegetables, Grains, and Beverages", *J. Agric. Food Chem*, 1981, pp. 1089-1091, Jun. 12, 1981.

International Search Report and Written Opinion, Int'l Application No. PCT/US2007/015600, date of mailing May 13, 2009.

Non-Final Office Action from the USPTO, U.S. Appl. No. 11/825,277, mailed Apr. 30, 2009.

Non-Final Office Action from the USPTO, U.S. Appl. No. 11/825,278, mailed Apr. 30, 2009.

* cited by examiner

FLAVORS FOR ORAL COMPOSITIONS

CROSS REFERENCE TO RELATED APPLICATION

This application claims the benefit of U.S. Provisional Application Nos. 60/819,154 and 60/819,156, both filed Jul. 7, 2006.

FIELD OF THE INVENTION

The present invention relates to aesthetically pleasing oral care formulations that contain flavor compositions and stannous ions.

BACKGROUND OF THE INVENTION

Stannous ions are desired to be used in oral compositions. Stannous ions, commonly supplied from stannous fluoride and other stannous salts, are used to provide anti-plaque, anti-gingivitis, and improve breath and sensitivity. However, formulating with stannous ions has proven to be challenging as formulations containing the stannous ions have been known to not be aesthetically pleasing. Stannous ions can provide a malodor when used in combination with certain oral care flavoring compounds. It remains desirable to provide oral care compositions that provide efficacious delivery of stannous ions with an aesthetically pleasing flavor. None of the existing art provides all of the aesthetic advantages and benefits of the present invention.

SUMMARY OF THE INVENTION

The present invention relates to oral care compositions comprising stannous ions, a mint-type flavor oil, a protectant component that prevents generation of malodor and off taste in the composition, and orally acceptable carriers. The mint-type oil includes peppermint, spearmint and corn mint. Suitable protectant components include carbonyl compounds such as ascorbic acid; cis-jasmone; 2,5-dimethyl-4-hydroxy-3(2H)-furanone; 5-ethyl-3-hydroxy-4-methyl-2(5H)-furanone; vanillin; ethyl vanillin; anisaldehyde; 3,4-methylenedioxybenzaldehyde; 3,4-dimethoxybenzaldehyde; 4-hydroxybenzaldehyde; 2-methoxybenzaldehyde; benzaldehyde; cinnamaldehyde; hexyl cinnamaldehyde; α-methyl cinnamaldehyde; ortho-methoxy cinnamaldehyde; α-amyl cinnamaldehyde; and combinations thereof.

These and other features, aspects, and advantages of the invention will become evident to those of skill in the art from a reading of the present disclosure.

DETAILED DESCRIPTION OF THE INVENTION

While the specification concludes with claims particularly pointing out and distinctly claiming the invention, it is believed that the present invention will be better understood from the following description of preferred embodiments.

All percentages used herein are by weight of the dentifrice composition, unless otherwise specified. The ratios used herein are molar ratios of the overall composition, unless otherwise specified. All measurements are made at 25° C., unless otherwise specified.

Herein, "comprising" means that other steps and other components which do not affect the end result can be added. This term encompasses the terms "consisting of" and "consisting essentially of."

As used herein, the word "include," and its variants, are intended to be non-limiting, such that recitation of items in a list is not to the exclusion of other like items that may also be useful in the materials, compositions, devices, and methods of this invention.

As used herein, the words "preferred", "preferably" and variants refer to embodiments of the invention that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

Herein, "effective amount" means an amount of a compound or composition sufficient to significantly induce a positive benefit, preferably an oral health benefit, but low enough to avoid serious side effects, i.e., to provide a reasonable benefit to risk ratio, within the sound judgment of a skilled artisan.

By "oral care composition" is meant a product, which in the ordinary course of usage, is not intentionally swallowed for purposes of systemic administration of particular therapeutic agents, but may be retained in the oral cavity for a time sufficient to contact substantially all of the dental surfaces and/or oral tissues for purposes of oral activity. The oral care composition may be in various forms including toothpaste, dentifrice, tooth gel, subgingival gel, mouthrinse, mousse, foam, denture care product, mouthspray, lozenge, chewable tablet or chewing gum. The oral care composition may also be incorporated onto strips or films for direct application or attachment to oral surfaces.

The term "dentifrice", as used herein, means paste, gel, or liquid formulations unless otherwise specified. The dentifrice composition may be a single phase composition or may be a combination of two or more separate dentifrice compositions. The dentifrice composition may be in any desired form, such as deep striped, surface striped, multilayered, having the gel surrounding the paste, or any combination thereof. Each dentifrice composition in a dentifrice comprising two or more separate dentifrice compositions may be contained in a physically separated compartment of a dispenser and dispensed side-by-side.

The term "dispenser", as used herein, means any pump, tube, or container suitable for dispensing compositions such as dentifrices.

The term "teeth", as used herein, refers to natural teeth as well as artificial teeth or dental prosthesis.

The term "flavor oils" refers to essential oils used as flavoring agents, which are volatile oils distilled or expressed from plants and constituents of these volatile oils. The term "flavor oils" as used herein when referring to mint and mint-type oils includes various grades of the oil typically referred to as prime natural or unfolded (freshly extracted from plant source) and refined or rectified to standardize the oil and remove unwanted flavor/odor characters (e.g., by fractional distillation). The rectified grade is generally the commercial grade supplied to end users for use as flavorings and perfumes. Typical essential oils and their main constituents are those obtained for example from thyme (thymol, carvacrol), oregano (carvacrol, terpenes), lemon (limonene, terpinene, phellandrene, pinene, citral), lemongrass (citral, methylheptenone, citronellal, geraniol), orange flower (linalool, β-pinene, limonene), orange (limonene, citral), anise (anethole, safrol), clove (eugenol, eugenyl acetate, caryophyllene), rose (geraniol, citronellol), rosemary (borneol, bornyl esters, camphor), geranium (geraniol, citronellol, linalool), lavender (linalyl acetate, linalool), citronella (geraniol, citronellol, citronellal, camphene), eucalyptus (eucalyptol); peppermint (menthol, menthyl esters), spearmint (carvone, limonene, pinene); wintergreen (methyl salicylate), camphor (safrole, acetaldehyde, camphor), bay (eugenol, myrcene, chavicol), cinnamon (cinnamaldehyde, cinnamyl acetate, eugenol), tea tree (terpinen-4-ol, cineole), and cedar leaf (α-thujone, β-thujone, fenchone). Essential oils, their composition and production, are described in detail in Kirk-Othmer *Encyclopedia of Chemical Technology*, $4^{th}$ Edition and in *The Merck Index*, $13^{th}$ Edition.

The term "orally acceptable carrier" includes safe and effective materials, excipients or additives used in oral care compositions including but not limited to fluoride ion sources, anti-calculus or anti-tartar agents, buffers, abrasives such as silica, alkali metal bicarbonate salts, thickening materials, humectants, water, surfactants, titanium dioxide, flavoring agents, sweetening agents, xylitol, coloring agents, and mixtures thereof.

Active and other ingredients useful herein may be categorized or described herein by their cosmetic and/or therapeutic benefit or their postulated mode of action or function. However, it is, to be understood that the active and other ingredients useful herein can, in some instances, provide more than one cosmetic and/or therapeutic benefit or function or operate via more than one mode of action. Therefore, classifications herein are made for the sake of convenience and are not intended to limit an ingredient to the particularly stated application or applications listed.

Herein, the terms "tartar" and "calculus" are used interchangeably and refer to mineralized dental plaque biofilms.

The present compositions comprise essential components, as well as optional components. The essential and optional components of the compositions of the present invention are described in the following paragraphs.

The present invention involves the discovery that the malodor found in stannous containing compositions occurs commonly when a mint oil, particularly a *Mentha* or *Mentha*-like essential oil, is present in the composition. The malodor can be described as an off-note or a "skunky" smell that also causes an off taste in the oral composition. Although select alternative flavors other than mint oils can be formulated with stannous and not form a malodor, a mint component in the flavor is commonly desired. It is even more desired that the oral composition has an overall minty taste in that mint is the most dominant flavor in the oral care composition. It has also been discovered that the main malodor precursor species present in flavor oils are sulfur-containing compounds such as dimethyl sulfoxide (DMSO), dimethyl sulfide (DMS), dimethyl disulfide and dimethyl sulfone, with samples having levels as high as 300 ppm or more. The following table shows levels of DMSO and DMS in spearmint and peppermint samples. As shown below, the main species is DMSO; significantly lower amounts of DMS are found in the flavor oils.

TABLE 1

DMSO and DMS Levels in Feedstock Peppermint and Spearmint Oils

| Sample | DMSO (ppm, w/v) | DMS (ppm, w/v) |
| --- | --- | --- |
| Peppermint Feedstock #1 | 318 | 10.3 |
| Peppermint Feedstock #2 | 312 | 22.1 |
| Peppermint Feedstock #3 | 181 | 46.8 |
| Spearmint (1% head cut) | 235 | <1 |

Peppermint oils supplied by I.P. Callison, Spearmint oil supplied by Labbeemint

The occurrence of DMSO in nature has been reported. For example, naturally occurring levels of DMSO in selected fruits, vegetables, grains and beverages are reported in *J. Agric. Food Chem.* 1981, 29, pp. 1089-91. The highest level reported was in black tea beverage with 16 ppm. In most samples, the level found was less than 1 ppm, with higher levels found in concentrated or processed samples such as tomato paste. It was thought that the increase in DMSO levels may be due to oxidation of dimethyl sulfide (DMS) during commercial processing. DMS is found extensively in nature and is responsible for the characteristic odor of many foods. DMSO was also reported to occur in spearmint oil [*Anais de Academia Brasileira de Ciencias*, 1972, 44 (Suppl.), 273-7] and in peppermint oil [*Agric. Biol. Chem.*, 1980, 44(7), 1535-43]. There have been no reports of the levels discovered in the mint flavor oils herein.

Not being bound by theory, it is believed that the sulfur-containing compounds in the mint oil, in particular DMSO, react with stannous ions and form species such as thiols or mercaptans responsible for the observed malodor and off-taste. Stannous ions have fairly strong reducing properties, being oxidized to stannic form when reacting with DMSO which in turn is reduced to the malodor species DMS and further to methyl mercaptan ($CH_3SH$). In order to prevent the malodor generation, one way is to clean-up the mint oils to remove the malodor precursors, such as described in the co-filed copending applications entitled "FLAVOR OILS WITH REDUCED SULFUR CONTENT AND USE IN ORAL CARE COMPOSITIONS". Alternatively, the present inventors have found that the malodor may be prevented by using certain "protectant" components, in combination with the mint oil. These protectants are compounds believed to act as traps that bind the malodorous sulfur species, thereby preventing the malodor. Advantageously, many of these protectants are also flavor ingredients and can thus be incorporated as part of the flavor system to also provide a particular flavor profile. The present flavor systems provide a full, well balanced flavor with a mint component can be used in stannous containing oral compositions without the malodor. The oral composition will have a mint dominant flavor without malodor or off taste.

Flavor System

The present flavor system comprises a mint oil, a protectant component and optionally other traditional flavor ingredients including sweeteners and coolants. One or more mint oils may be present. One or more protectants may be used. Other flavor components, such as coolants or other flavors, may also be used to form the flavor system. The flavor system is typically present in an oral composition in an amount of from about 0.01% to about 5%, by weight of the composition. Preferably, the flavor system is present from about 0.02% to about 4%, more preferably from about 0.1% to about 3%, and most preferably from about 0.5% to about 2% by weight of the composition. The components of the flavor system are described below.

Mint Oils

Mint oils include those designated as a *Mentha* species essential oil, such as *piperita* or *arvensis, spicata, cardiaca* or *viridis Crispa*. The mint oils include those commonly known as peppermint, corn mint and spearmint. The mint oil may be natural or synthetic or a combination of natural and synthetic components. The mint oil can be fractionated or rectified using standard distillation and/or extraction equipment to remove any non-desired components. The mint oil is typically present in an amount of from 2-1300 ppm.

Protectant Component

Suitable protectant components include copper salts and carbonyl compounds such as ascorbic acid [3-oxo-L-gulo-furanolactone]; cis-jasmone [3-methyl-2-(2-pentenyl-2-cyclopentenone]; 2,5-dimethyl-4-hydroxy-3(2H)-furanone; 5-ethyl-3-hydroxy-4-methyl-2(5H)-furanone; vanillin [4-hydroxy-3-methoxybenzaldehyde]; ethyl vanillin; anisaldehyde [4-methoxybenzaldehyde]; 3,4-methylenedioxybenzaldehyde; 3,4-dimethoxybenzaldehyde; 4-hydroxybenzaldehyde; 2-methoxybenzaldehyde; benzaldehyde; cinnamaldehyde [3-phenyl-2-propenal]; hexyl cinnamaldehyde; α-methyl cinnamaldehyde; ortho-methoxy cinnamaldehyde; α-amyl cinnamaldehyde; and combinations thereof.

There main mechanisms believed to operate in reduction of volatile malodorous sulfur compounds, such as methyl mercaptan (a thiol) and dimethyl sulfide (DMS) via the use of the above protectants are illustrated in the chemical reactions below. The protectants act as "traps" by reacting with the thiol or sulfide and forming products with less odor impact. The reactions involving carbonyl compounds are as follows:

a) Michael reaction of thiols or alkyl sulfides with Michael acceptors, i.e., α,β-unsaturated carbonyl compounds to give addition compounds as shown below which are likely to be less volatile or nonvolatile and hence less odoriferous.

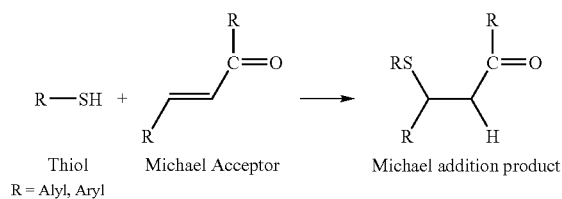

Thiol    Michael Acceptor    Michael addition product
R = Alyl, Aryl b) Ketones and aldehydes can react with thiols to give thio ketals and thio acetals as follows:

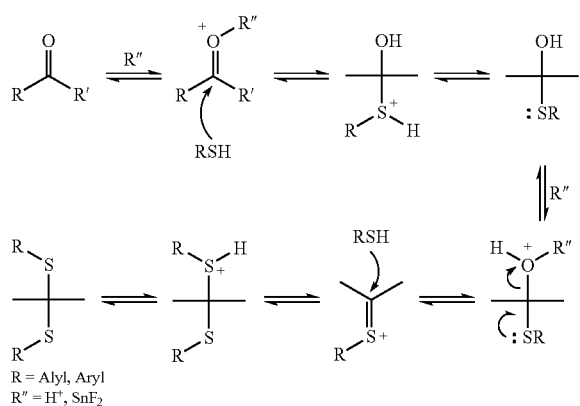

R = Alyl, Aryl
R" = H$^+$, SnF$_2$

To study the effects of protectants on malodor production in systems containing stannous fluoride and natural peppermint oil, 20-mL glass vials were prepared to contain 3 mL rectified peppermint oil (supplied by I.P. Callison), 3 mL water, and 225 mg of stannous fluoride. To all vials, except control, a protectant was added at 1% (v/v) of the amount of peppermint oil. Capped vials were stored at 50° C. for 72 hours. After equilibrating at room temperature, the headspace of the each vial was sampled with a solid phase microextraction (SPME) fiber. For samples taken from each vial, the SPME fiber was desorbed in a GC inlet; the volatiles were separated on a GC column; and the effluent was analyzed with a sulfur chemiluminescence detector (SCD). Peak areas of methyl mercaptan (MM) and dimethyl sulfide (DMS) were evaluated relative to the control levels of these compounds and, as shown on the table below, the protectants caused a substantial reduction in the measured levels of the malodor compounds MM and DMS in stannous fluoride/peppermint oil mixtures.

| Protectant | MM Normalized to Control | DMS Normalized to Control |
| --- | --- | --- |
| None (Control) | 100 | 100 |
| trans-Cinnamaldehyde | 41 | 55 |
| 4-Methoxybenzaldehyde | 31 | 4 |
| cis-Jasmone | 56 | 78 |
| Ascorbic acid | 43 | 33 |
| 2,5-Dimethyl-4-hydroxy-3(2H) furanone | 14 | 6 |
| 5-Ethyl-3-hydroxy-4-methyl-2(5H) furanone | 51 | 39 |
| Ethyl vanillin | 31 | 41 |

The amount of protectant component depends upon the specific protectant chosen, the specific mint oil and amount chosen, the amount of stannous ions, other flavor components added, and the desired flavor profile in the oral composition. Some of the protectants have flavoring properties and will provide flavor characters such as vanilla, smooth creamy or cinnamon. Each of these protectants can be used alone or with other protectants. The ratio of protectant to mint oil that has been found to be effective is from about 2:1 to about 1:300 by weight. Preferably, when using protectants such as ascorbic acid, cis-jasmone, 2,5-dimethyl-4-hydroxy-3(2H)-furanone, 5-ethyl-3-hydroxy-4-methyl-2(5H)-furanone, ethyl vanillin, vanillin, anisaldehyde, 3,4-methylenedioxybenzaldehyde, 3,4-dimethoxybenzaldehyde, 4-hydroxybenzaldehyde or 2-methoxybenzaldehyde, the ratio is from about 1:1 to about 1:200. For any of the cinnamaldehyde compounds, the ratio of protectant to mint oil is preferably from about 1:2 to about 1:16 by weight, more preferably from about 1:3 to about 1:12. At high ratios of protectant to mint oil, the non-mint flavor may dominate.

Typical concentrations of protectant(s) in oral compositions containing stannous ions is in the range of: 13-2000 ppm of cis-jasmone; 2,5-dimethyl-4-hydroxy-3(2H)-furanone; 5-ethyl-3-hydroxy-4-methyl-2(5H)-furanone; ethyl vanillin or vanillin; 6-700 ppm anisaldehyde; 3,4-methylenedioxybenzaldehyde; 3,4-dimethoxybenzaldehyde; 4-hydroxybenzaldehyde; or 2-methoxybenzaldehyde; 10-100 ppm benzaldehyde; 200-2700 ppm cinnamaldehyde; hexyl cinnamaldehyde; α-methyl cinnamaldehyde; ortho-methoxy cinnamaldehyde; or α-amyl cinnamaldehyde.

In addition to the mint oil(s) and protectant(s), the flavor system may comprise additional flavor ingredients including but not limited to oil of wintergreen, clove bud oil, cassia, sage, parsley oil, marjoram, lemon, orange, propenyl guaethol, heliotropine, 4-cis-heptenal, diacetyl, methyl-p-tert-butyl phenyl acetate, menthol, methyl salicylate, ethyl salicylate, 1-menthyl acetate, oxanone, α-irisone, methyl cinnamate, ethyl cinnamate, butyl cinnamate, ethyl butyrate, ethyl acetate, methyl anthranilate, iso-amyl acetate, iso-amyl butyrate, allyl caproate, eugenol, eucalyptol, thymol, cinnamic alcohol, octanol, octanal, decanol, decanal, phenylethyl alcohol, benzyl alcohol, α-terpineol, linalool, limonene, citral, maltol, ethyl maltol, anethole, dihydroanethole, carvone, menthone, β-damascenone, ionone, γ-decalactone, γ-nonalactone, γ-undecalactone and mixtures thereof. Generally suitable flavoring ingredients are chemicals with structural features and functional groups that are less prone to redox reactions. These include derivatives of flavor chemicals that are saturated or contain stable aromatic rings or ester groups. Also suitable are flavor chemicals that may undergo some oxidation or degradation without resulting in a significant change in the flavor character or profile. The flavor ingredients may be provided as single or purified chemicals or supplied in the composition by addition of natural oils or extracts that have preferably undergone some refining treatment to remove components that are relatively unstable and may degrade and alter the desired flavor profile, resulting in a less acceptable product from an organoleptic standpoint.

The flavor system may further comprise cooling agents or coolants such as menthol, menthyl esters, carboxamides, ketals, diols, and mixtures thereof. Examples of suitable coolants useful in the present compositions are the paramenthan carboxamide agents such as N-ethyl-p-menthan-3-carboxamide, known commercially as "WS-3"; N,2,3-trimethyl-2-isopropylbutanamide, known as "WS-23"; N-ρ-benzeneacetonitrile-menthanecarboxamide; and others in the series such as WS-5, WS-11, WS-14 and WS-30. Additional suitable coolants include 3-1-menthoxypropane-1,2-diol known as TK-10 manufactured by Takasago; menthone glycerol acetal (Frescolat® MGA); menthyl esters such as menthyl acetate, menthyl acetoacetate, menthyl lactate (Frescolat® ML supplied by Haarmann and Reimer), and monomenthyl succinate (under the tradename Physcool from V. Mane). The terms menthol and menthyl as used herein include dextro- and levorotatory isomers of these compounds and racemic mixtures thereof. TK-10 is described in U.S. Pat. No. 4,459,425, Amano et al., issued Jul. 10, 1984. WS-3 and other agents are described in U.S. Pat. No. 4,136,163, Watson, et al., issued Jan. 23, 1979.

The flavor system will typically include a sweetening agent. Suitable sweeteners include those well known in the art, including both natural and artificial sweeteners. Some suitable water-soluble sweeteners include monosaccharides, disaccharides, polysaccharides and derivatives such as xylose, ribose, glucose (dextrose), mannose, galactose, fructose (levulose), sucrose (sugar), maltose, invert sugar (a mixture of fructose and glucose derived from sucrose), partially hydrolyzed starch, corn syrup solids, dihydrochalcones, monellin, steviosides, glycyrrhizin, xylitol and erythritol. Suitable water-soluble artificial sweeteners include soluble saccharin salts, i.e., sodium or calcium saccharin salts, cyclamate salts, the sodium, ammonium or calcium salt of 3,4-dihydro-6-methyl-1,2,3-oxathiazine-4-one-2,2-dioxide, the potassium salt of 3,4-dihydro-6-methyl-1,2,3-oxathiazine-4-one-2,2-dioxide (acesulfame-K), the free acid form of saccharin, and the like. Other suitable sweeteners include dipeptide based sweeteners, such as L-aspartic acid derived sweeteners, such as L-aspartyl-L-phenylalanine methyl ester (aspartame) and materials described in U.S. Pat. No. 3,492,131, L-alpha-aspartyl-N-(2,2,4,4-tetramethyl-3-thietanyl)-D-alaninamide hydrate, methyl esters of L-aspartyl-L-phenylglycerin and L-aspartyl-L-2,5,dihydrophenyl-glycine, L-aspartyl-2,5-dihydro-L-phenylalanine, L-aspartyl-L-(1-cyclohexyen)-alanine, and the like. Water-soluble sweeteners derived from naturally occurring water-soluble sweeteners, such as a chlorinated derivative of ordinary sugar (sucrose), known, for example, under the product description of sucralose as well as protein based sweeteners such as *thaumatococus danielli* (Thaumatin I and II) can be used. The composition preferably contains from about 0.1% to about 10% of sweetener, preferably from about 0.1% to about 1%, by weight.

In addition the flavor system may include salivating agents, warming agents, and numbing agents. These agents are present in the compositions at a level of from about 0.001% to about 10%, preferably from about 0.1% to about 1%, by weight of the composition. Suitable salivating agents include Jambu® manufactured by Takasago. Examples of warming agents are capsicum and nicotinate esters, such as benzyl nicotinate. Suitable numbing agents include benzocaine, lidocaine, clove bud oil, and ethanol.

Stannous Ions

The present invention also comprises stannous ions. The stannous ions are from a stannous source that can be soluble or sparingly soluble stannous compound. Examples include fluoride, chloride, chlorofluoride, acetate, hexafluorozirconate, sulfate, tartrate, gluconate, citrate, malate, glycinate, pyrophosphate, metaphosphate, oxalate, phosphate, carbonate salts and oxides of stannous. The stannous ions are typically present in an amount of at least about 1000 ppm stannous, preferably from about 2,000 ppm to about 15,000 ppm. More preferably, stannous ions are present from about 3,000 ppm to about 13,000 ppm. This is the total mount of stannous ions that is present in the composition for delivery to the tooth surface. The stannous ion source is typically present in an amount of from about 0.25% to about 11% by weight of the final composition. Preferably, the stannous ion source is present in an amount of from about 0.4% to about 7% and more preferably from about 0.45% to about 5%.

The stannous ion source is preferably not fully ionized in the composition during storage, prior to actual using of the composition. When the composition is contacted by saliva and/or water at the time of brushing, the stannous ion source will be fully ionized and the active ion will be delivered to the oral cavity. Dentifrices containing stannous salts, particularly stannous fluoride and stannous chloride, are described in U.S. Pat. No. 5,004,597 to Majeti et al. Other descriptions of stannous salt dentifrices are found in U.S. Pat. No. 5,578,293. The preferred stannous salt is stannous fluoride. Other suitable stannous salts include stannous chloride dihydrate, stannous acetate, stannous tartrate, and sodium stannous citrate.

Orally Acceptable Carrier Materials

Orally acceptable carriers are described below. They include any materials safe for oral compositions. The carrier materials may be active agents or non-active agents. Suitable carrier materials will preferably be essentially free of sulfur-compounds that are precursors of malodorous species.

Optional Active Agents

1. Teeth Whitening Actives

Teeth whitening actives may be included in the oral care substance of the present invention. The actives suitable for whitening are selected from the group consisting of the peroxides, metal chlorites, perborates, percarbonates, peroxyacids, persulfates, and combinations thereof. Suitable peroxide compounds include hydrogen peroxide, urea peroxide, calcium peroxide, and mixtures thereof. Suitable metal chlorites include calcium chlorite, barium chlorite, magnesium chlorite, lithium chlorite, sodium chlorite, and potassium chlorite. Additional whitening actives may be hypochlorite and chlorine dioxide. A preferred percarbonate is sodium percarbonate. Preferred persulfates are oxones.

2. Anti-Tartar Agents

Anti-tartar agents known for use in dental care products include phosphates. Phosphates include pyrophosphates, polyphosphates, polyphosphonates and mixtures thereof. Pyrophosphates are among the best known for use in dental care products. Pyrophosphate and polyphosphate ions are delivered to the teeth derive from pyrophosphate or polyphosphate salts. The pyrophosphate salts useful in the present compositions include the dialkali metal pyrophosphate salts, tetra-alkali metal pyrophosphate salts, and mixtures thereof. Disodium dihydrogen pyrophosphate ($Na_2H_2P_2O_7$), tetrasodium pyrophosphate ($Na_4P_2O_7$), and tetrapotassium pyrophosphate ($K_4P_2O_7$) in their unhydrated as well as hydrated forms are the preferred species. While any of the above mentioned pyrophosphate salts may be used, tetrasodium pyrophosphate salt is preferred. Sodium polyphosphate and triethanolamine polyphosphates, for example, are also useful.

The pyrophosphate salts are described in more detail in Kirk & Othmer, *Encyclopedia of Chemical Technology*, Third Edition, Volume 17, Wiley-Interscience Publishers (1982). Additional anticalculus agents include pyrophosphates or polyphosphates disclosed in U.S. Pat. No. 4,590,066 issued May 20, 1986; polyacrylates and other polycarboxylates such as those disclosed in U.S. Pat. No. 3,429,963 issued Feb. 25, 1969 and U.S. Pat. No. 4,304,766 issued Dec. 8, 1981; and U.S. Pat. No. 4,661,341 issued Apr. 28, 1987; polyepoxysuccinates such as those disclosed in U.S. Pat. No. 4,846,650 issued Jul. 11, 1989; ethylenediaminetetraacetic acid as disclosed in British Patent No. 490,384 dated Feb. 15, 1937; nitrilotriacetic acid and related compounds as disclosed in U.S. Pat. No. 3,678,154 issued Jul. 18, 1972; polyphosphonates as disclosed in U.S. Pat. No. 3,737,533 issued Jun. 5, 1973, U.S. Pat. No. 3,988,443 issued Oct. 26, 1976 and U.S. Pat. No. 4,877,603 issued Oct. 31, 1989.

Other anticalculus agents that may be used in place of or in combination with the pyrophosphate salt include such known materials as synthetic anionic polymers including polyacrylates and copolymers of maleic anhydride or acid and methyl vinyl ether (e.g., Gantrez), as described, for example, in U.S. Pat. No. 4,627,977; as well as, e.g., polyamino propane sulfonic acid (AMPS), zinc citrate trihydrate, polyphosphates (e.g., tripolyphosphate; hexametaphosphate), diphosphonates (e.g., EHDP; AHP), polypeptides (such as polyaspartic and polyglutamic acids), and mixtures thereof.

3. Fluoride Ion Source

Fluoride ion sources are well known for use in oral care compositions as anticaries agents. Fluoride ions are contained in a number of oral care compositions for this purpose, particularly toothpastes. Patents disclosing such toothpastes include U.S. Pat. Nos. 3,538,230, Nov. 3, 1970; 3,689,637, Sep. 5, 1972; 3,711,604, Jan. 16, 1973; 3,911,104, Oct. 7, 1975; 3,935,306, Jan. 27, 1976; and 4,040,858, Aug. 9, 1977.

Application of fluoride ions to dental enamel serves to protect teeth against decay. A wide variety of fluoride ion-yielding materials can be employed as sources of soluble fluoride in the instant compositions. Examples of suitable fluoride ion-yielding materials are found in U.S. Pat. No. 3,535,421; issued Oct. 20, 1970 and U.S. Pat. No. 3,678,154; issued Jul. 18, 1972, such as sodium fluoride, potassium fluoride, stannous fluoride and ammonium fluoride. In one embodiment, the instant compositions provide from about 50 ppm to 10,000 ppm; in another embodiment from about 100 to 3000 ppm, of fluoride ions in the compositions that contact dental surfaces when used with the delivery system of the present invention.

4. Anti-Microbial Agents

Anti-microbial agents can also be present in the oral care compositions or substances of the present invention. Such agents may include, but are not limited to, 5-chloro-2-(2,4-dichlorophenoxy)-phenol, commonly referred to as triclosan, and described in *The Merck Index*, 11th ed. (1989), pp. 1529 (entry no. 9573) in U.S. Pat. No. 3,506,720, and in European Patent Application No. 0,251,591, published Jan. 7, 1988; phthalic acid and its salts including, but not limited to those disclosed in U.S. Pat. No. 4,994,262, Feb. 19, 1991, preferably magnesium monopotassium phthalate, chlorhexidine (*Merck Index*, no. 2090), alexidine (*Merck Index*, no. 222; hexetidine (*Merck Index*, no. 4624); sanguinarine (*Merck Index*, no. 8320); benzalkonium chloride (*Merck Index*, no. 1066); salicylanilide (*Merck Index*, no. 8299); domiphen bromide (*Merck Index*, no. 3411); cetylpyridinium chloride (CPC) (*Merck Index*, no. 2024); tetradecylpyridinium chloride (TPC); N-tetradecyl-4-ethylpyridinium chloride (TDEPC); octenidine; delmopinol, octapinol, and other piperidino derivatives; nicin preparations; zinc/stannous/copper ion agents; antibiotics such as augmentin, amoxicillin, tetracycline, doxycycline, minocycline, and metronidazole; and analogs and salts of the above; essential oils including thymol, geraniol, carvacrol, citral, hinokitiol, eucalyptol, catechol (particularly 4-allyl catechol) and mixtures thereof; methyl salicylate; hydrogen peroxide; metal salts of chlorite and mixtures of the above.

5. Anti-Inflammatory Agents

Anti-inflammatory agents can also be present in the oral care compositions or substances of the present invention. Such agents may include, but are not limited to, non-steroidal anti-inflammatory agents or NSAIDs such as ketorolac, flurbiprofen, ibuprofen, naproxen, indomethacin, aspirin, ketoprofen, piroxicam and meclofenamic acid. Use of NSAIDs such as ketorolac are claimed in U.S. Pat. No. 5,626,838, issued May 6, 1997. Disclosed therein are methods of preventing and, or treating primary and reoccurring squamous cell carcinoma of the oral cavity or oropharynx by topical administration to the oral cavity or oropharynx an effective amount of an NSAID.

6. Nutrients

Nutrients may improve the condition of the oral cavity and can be included in the oral care compositions or substances of the present invention. Nutrients include minerals, vitamins, oral nutritional supplements, enteral nutritional supplements, and mixtures thereof.

Minerals that can be included with the compositions of the present invention include calcium, phosphorus, fluoride, zinc, manganese, potassium and mixtures thereof. These minerals are disclosed in *Drug Facts and Comparisons* (loose leaf drug information service), Wolters Kluer Company, St. Louis, Mo., ©1997, pp 10-17.

Vitamins can be included with minerals or used separately. Vitamins include Vitamins C D and E, thiamine, riboflavin, calcium pantothenate, niacin, folic acid, nicotinamide, pyridoxine, cyanocobalamin, para-aminobenzoic acid, bioflavonoids, and mixtures thereof. Such vitamins are disclosed in *Drug Facts and Comparisons*, Wolters Kluer Company, ©1997, pp. 3-10.

Oral nutritional supplements include amino acids, lipotropics, fish oil, and mixtures thereof, as disclosed in *Drug Facts and Comparisons*, Wolters Kluer Company, © 1997, pp. 54-54e. Amino acids include, but, are not limited to L-Tryptophan, L-Lysine, Methionine, Threonine, Levocarnitine or L-carnitine and mixtures thereof. Lipotropics include, but, are not limited to choline, inositol, betaine, linoleic acid, linolenic acid, and mixtures thereof. Fish oil contains large amounts of Omega-3 (N-3) Polyunsaturated fatty acids, eicosapentaenoic acid and docosahexaenoic acid.

Enteral nutritional supplements include, but, are not limited to protein products, glucose polymers, corn oil, safflower oil, medium chain triglycerides as disclosed in *Drug Facts and Comparisons*, Wolters Kluer Company,® 1997, pp. 55-57.

7. Mouth and Throat Products

Other materials that can be used with the present invention include commonly known mouth and throat products. Such products are disclosed in *Drug Facts and Comparisons*, Wolters Kluer Company, St. Louis, Mo., ©1997, pp. 520b-527. These products include, but, are not limited to antifungal, antibiotic and analgesic agents.

8. Antioxidants

Antioxidants are generally recognized as useful in compositions such as those of the present invention. Antioxidants are disclosed in texts such as Cadenas and Packer, *The Handbook of Antioxidants*, © 1996 by Marcel Dekker, Inc. Antioxidants that may be included in the oral care composition or substance of the present invention include, but are not limited to Vitamin E, ascorbic acid, Uric acid, carotenoids, Vitamin A, flavonoids and polyphenols, herbal antioxidants, melatonin, aminoindoles, lipoic acids and mixtures thereof.

9. H-2 Antagonists

Histamine-2 (H-2 or H2) receptor antagonist compounds (H-2 antagonists) may be used in the oral care composition of the present invention. As used herein, selective H-2 antagonists are compounds that block H-2 receptors, but do not have meaningful activity in blocking histamine-1 (H-1 or H1) receptors. Selective H-2 antagonists include compounds meeting the above criteria which are disclosed in U.S. Pat. Nos. 5,294,433 and 5,364,616, issued Mar. 15, 1994 and Nov. 15, 1994 respectively and assigned to Procter & Gamble.

10. Analgesic Actives

Anti-pain or desensitizing agents can also be present in the oral care compositions or substances of the present invention. Such agents may include, but are not limited to, strontium chloride, potassium nitrate, natural herbs such as gall nut, Asarum, Cubebin, Galanga, scutellaria, Liangmianzhen, Baizhi, etc.

11. Anti-Viral Actives

Antiviral actives useful in the present composition include any know actives that are routinely use to treat viral infections. Such anti-viral actives are disclosed in *Drug Facts and Comparisons*, Wolters Kluer Company, ©1997, pp. 402(a)-407(z). Specific examples include anti-viral actives disclosed in U.S. Pat. No. 5,747,070, issued May 5, 1998. This patent discloses the use of stannous salts to control viruses. Stannous salts and other anti-viral actives are described in detail in Kirk & Othmer, *Encyclopedia of Chemical Technology*, Third Edition, Volume 23, Wiley-Interscience Publishers (1982), pp. 42-71. The stannous salts that may be used in the present invention would include organic stannous carboxylates and inorganic stannous halides. While stannous fluoride may be used, it is typically used only in combination with another stannous halide or one or more stannous carboxylates or another therapeutic agent.

12. Phenolics

Phenolics and derivatives from plant sources such as tea, cranberry, pomegranate and oak bark may also be incorporated in the present compositions, for their utility as antimicrobial, anti-inflammatory and antioxidant activities. Many of these phenolics and derivatives are also useful as flavoring agents. Such phenolics include catechin, gallocatechin gallate, epicatechin (EC), epigallocatechin (EGC), epigallocatechin gallate (EGCG), epicatechin gallate (ECG), theaflavine, thearubigins, anthocyanidins/proanthocyanidins and anthocyanins (e.g., cyanidin, delphinidin, pelargonidin, peonidin, malvidin and petunidin); tannic acid; gallic acid; ellagic acid; ellagitannins; curcumin. The phenolics may be supplied as purified compounds or as plant extracts. Phenolics useful as oral care actives are disclosed in commonly assigned U.S. patent application Ser. No. 11/595,530, published as US 2007/0053849A1.

Many of the phenolics used in oral care compositions as actives or flavor agents are susceptible to oxidation, i.e., have reducing capability and can thus react with DMSO in the same manner as stannous producing malodorous sulfur species.

Other Agents

In addition to the above materials, a number of other components may desirably be added.

1. Water

The present compositions range from substantially non-aqueous to aqueous. By substantially non-aqueous is meant that the compositions may contain very low amounts of water, less than about 5%, which is typically introduced in the composition with other materials, such as with sorbitol or other hygroscopic materials. Water employed in the preparation of commercially suitable aqueous compositions should preferably be of low ion content and free of organic impurities. Water generally comprises from about 5% to about 70%, and preferably from about 20% to about 50%, by weight of the aqueous compositions herein. These amounts of water include the free water which is added plus that which is introduced with other materials.

2. Binder System

The dentifrice compositions of the present invention incorporate a binder system comprised of a thickening agent selected from the group consisting of polysaccharides, carbomers, poloxamers, modified celluloses, and mixtures thereof, and at least one humectant. The thickening agent comprises from about 0.05% to about 3%, and preferably from about 0.1% to 1.5%, by weight of the composition. These binder systems provide desirable consistency and gellation to the composition. The binder system may further comprise additional inorganic thickening agents. The humectant serves to keep toothpaste compositions from hardening upon exposure to air and certain humectants can also impart desirable sweetness of flavor to toothpaste compositions. Suitable humectants for use in the invention include glycerin, sorbitol, polyethylene glycol, propylene glycol, xylitol, and other edible polyhydric alcohols. Preferred are glycerin, polyethylene glycol, polypropylene glycol, and mixtures thereof, especially mixtures thereof. The humectant generally comprises from about 0.1% to 70%, preferably from about 1% to about 60%, and more preferably from about 15% to 55%, by weight of the composition.

The binder system may further comprise additional inorganic thickening agents such as colloidal magnesium aluminum silicate or finely divided silica to further improve texture. Additional inorganic thickening agents if present can be used in an amount from about 0.1% to about 15%, more preferably from about 0.1% to about 5%, by weight of the dentifrice composition.

3. Buffering Agents

The present compositions may contain a buffering agent. Buffering agents, as used herein, refer to agents that can be used to adjust the pH of the compositions to a range of about pH 3.0 to about pH 10. The buffering agents include alkali metal hydroxides, ammonium hydroxide, organic ammonium compounds, carbonates, sesquicarbonates, borates, silicates, phosphates, imidazole, and mixtures thereof. Specific buffering agents include monosodium phosphate, trisodium phosphate, sodium benzoate, benzoic acid, sodium hydroxide, potassium hydroxide, alkali metal carbonate salts, sodium carbonate, imidazole, pyrophosphate salts, citric acid, and sodium citrate. Buffering agents are used at a level of from about 0.1% to about 30%, preferably from about 0.1% to about 10%, and more preferably from about 0.3% to about 3%, by weight of the present composition.

4. Abrasive Polishing Materials

An abrasive polishing material may also be included in the toothpaste compositions. The abrasive polishing material contemplated for use in the compositions of the present invention can be any material that does not excessively abrade dentin. Typical abrasive polishing materials include silicas including gels and precipitates; aluminas; phosphates including orthophosphates, polymetaphosphates, and pyrophosphates; and mixtures thereof. Specific examples include dicalcium orthophosphate dihydrate, calcium pyrophosphate, tricalcium phosphate, calcium polymetaphosphate, insoluble sodium polymetaphosphate, hydrated alumina, beta calcium pyrophosphate, calcium carbonate, and resinous abrasive materials such as particulate condensation products of urea and formaldehyde, and others such as disclosed by Cooley et al in U.S. Pat. No. 3,070,510, issued Dec. 25, 1962. Mixtures of abrasives may also be used. If the dentifrice composition or particular phase comprises a polyphosphate having an average chain length of about 4 or more, calcium containing abrasives and alumina are not preferred abrasives. The most preferred abrasive is silica.

Silica dental abrasives of various types are preferred because of their unique benefits of exceptional dental cleaning and polishing performance without unduly abrading tooth enamel or dentine. The silica abrasive polishing materials herein, as well as other abrasives, generally have an average particle size ranging between about 0.1 to about 30 microns, and preferably from about 5 to about 15 microns. The abrasive can be precipitated silica or silica gels such as the silica xerogels described in Pader et al., U.S. Pat. No. 3,538,230, issued Mar. 2, 1970, and DiGiulio, U.S. Pat. No. 3,862,307, issued Jan. 21, 1975. Examples include the silica xerogels marketed under the trade name "Syloid" by the W.R. Grace & Company, Davison Chemical Division and precipitated silica materials such as those marketed by the J. M. Huber Corporation under the trade name, Zeodent®, particularly the silicas carrying the designation Zeodent® 119, Zeodent® 118, Zeodent® 109 and Zeodent® 129. The types of silica dental abrasives useful in the toothpastes of the present invention are described in more detail in Wason, U.S. Pat. No. 4,340,583, issued Jul. 29, 1982; and in commonly-assigned U.S. Pat. Nos. 5,603,920; 5,589,160; 5,658,553; 5,651,958; 5,716,601 and 6,740,311.

Mixtures of abrasives can be used such as mixtures of the various grades of Zeodent® silica abrasives listed above. The total amount of abrasive in dentifrice compositions of the subject invention typically range from about 6% to about 70% by weight; toothpastes preferably contain from about 10% to about 50% of abrasives, by weight of the composition. Dental solution, mouth spray, mouthwash and non-abrasive gel compositions of the subject invention typically contain little or no abrasive.

4. Tooth Substantive Agent

The present invention may include a tooth substantive agent such as polymeric surface active agents (PMSA's), which are polyelectrolytes, more specifically anionic polymers. The PMSA's contain anionic groups, e.g., phosphate, phosphonate, carboxy, or mixtures thereof, and thus, have the capability to interact with cationic or positively charged entities. The "mineral" descriptor is intended to convey that the surface activity or substantivity of the polymer is toward mineral surfaces such as calcium phosphate minerals or teeth.

PMSA's are useful in the present compositions because of their stain prevention benefit. It is believed the PMSA's provide a stain prevention benefit because of their reactivity or substantivity to mineral surfaces, resulting in desorption of portions of undesirable adsorbed pellicle proteins, in particular those associated with binding color bodies that stain teeth, calculus development and attraction of undesirable microbial species. The retention of these PMSA's on teeth can also prevent stains from accruing due to disruption of binding sites of color bodies on tooth surfaces.

The ability of PMSA's to bind stain promoting ingredients of oral care products such as stannous ions and cationic antimicrobials is also believed to be helpful. The PMSA will also provide tooth surface conditioning effects which produce desirable effects on surface thermodynamic properties and surface film properties, which impart improved clean feel aesthetics both during and most importantly, following rinsing or brushing. Many of these polymeric agents are also known or expected to provide tartar control benefits when applied in oral compositions, hence providing improvement in both the appearance of teeth and their tactile impression to consumers.

The desired surface effects include: 1) creating a hydrophilic tooth surface immediately after treatment; and 2) maintaining surface conditioning effects and control of pellicle film for extended periods following product use, including post brushing or rinsing and throughout more extended periods. The effect of creating an increased hydrophilic surface can be measured in terms of a relative decrease in water contact angles. The hydrophilic surface, importantly, is maintained on the tooth surface for an extended period after using the product.

The polymeric mineral surface active agents include any agent which will have a strong affinity for the tooth surface, deposit a polymer layer or coating on the tooth surface and produce the desired surface modification effects. Suitable examples of such polymers are polyelectrolytes such as condensed phosphorylated polymers; polyphosphonates; copolymers of phosphate- or phosphonate-containing monomers or polymers with other monomers such as ethylenically unsaturated monomers and amino acids or with other polymers such as proteins, polypeptides, polysaccharides, poly (acrylate), poly(acrylamide), poly(methacrylate), poly (ethacrylate), poly(hydroxyalkylmethacrylate), poly(vinyl alcohol), poly(maleic anhydride), poly(maleate) poly (amide), poly(ethylene amine), poly(ethylene glycol), poly (propylene glycol), poly(vinyl acetate) and poly(vinyl benzyl chloride); polycarboxylates and carboxy-substituted polymers; and mixtures thereof. Suitable polymeric mineral surface active agents include the carboxy-substituted alcohol polymers described in U.S. Pat. Nos. 5,292,501; 5,213,789, 5,093,170; 5,009,882; and 4,939,284; all to Degenhardt et al. and the diphosphonate-derivatized polymers in U.S. Pat. No. 5,011,913 to Benedict et al; the synthetic anionic polymers including polyacrylates and copolymers of maleic anhydride or acid and methyl vinyl ether (e.g., Gantrez), as described, for example, in U.S. Pat. No. 4,627,977, to Gaffar et al. A preferred polymer is diphosphonate modified polyacrylic acid. Polymers with activity must have sufficient surface binding propensity to desorb pellicle proteins and remain affixed to enamel surfaces. For tooth surfaces, polymers with end or side chain phosphate or phosphonate functions are preferred although other polymers with mineral binding activity may prove effective depending upon adsorption affinity. Additional examples of suitable phosphonate containing polymeric mineral surface active agents include the geminal diphosphonate polymers disclosed as anticalculus agents in U.S. Pat. No. 4,877,603 to Degenhardt et al; phosphonate group containing copolymers disclosed in U.S. Pat. No. 4,749,758 to Dursch et al. and in GB 1,290,724 (both assigned to Hoechst) suitable for use in detergent and cleaning compositions; and the copolymers and cotelomers disclosed as useful for applications including scale and corrosion inhibition, coatings, cements and ion-exchange resins in U.S. Pat. No. 5,980,776 to Zakikhani et al. and U.S. Pat. No. 6,071,434 to Davis et al. Additional polymers include the water-soluble copolymers of vinylphosphonic acid and acrylic acid and salts thereof disclosed in GB 1,290,724 wherein the copolymers contain from about 10% to about 90% by weight vinylphosphonic acid and from about 90% to about 10% by weight acrylic acid, more particularly wherein the copolymers have a weight ratio of vinylphosphonic acid to acrylic acid of 70% vinylphosphonic acid to 30% acrylic acid; 50% vinylphosphonic acid to 50% acrylic acid; or 30% vinylphosphonic acid to 70% acrylic acid. Other suitable polymers include the water soluble polymers disclosed by Zakikhani and Davis prepared by copolymerizing diphosphonate or polyphosphonate monomers having one or more unsaturated C=C bonds (e.g., vinylidene-1,1-diphosphonic acid and 2-(hydroxyphosphinyl)ethylidene-1,1-diphosphonic acid), with at least one further compound having unsaturated C=C bonds (e.g., acrylate and methacrylate monomers), such as those having the following structure:

1. Co-telomer of acrylic acid and 2-(hydroxyphosphinyl)ethylidene-1,1-diphosphonic acid with structure:

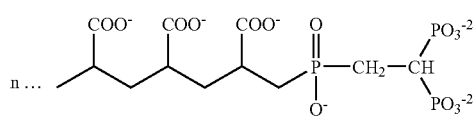

2. Co-polymer of acrylic acid and vinyldiphosphonic acid with structure:

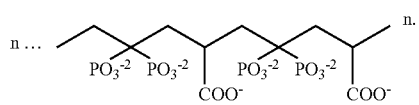

Suitable polymers include the diphosphonate/acrylate polymers supplied by Rhodia under the designation ITC 1087 (Average MW 3000-60,000) and Polymer 1154 (Average MW 6000-55,000).

A preferred PMSA will be stable with other components of the oral care composition such as ionic fluoride and metal ions. Also preferred are polymers that have limited hydrolysis in high water content formulations, thus permitting a simple single phase dentifrice or mouthrinse formulation. If the PMSA does not have these stability properties, one option is a dual phase formulation with the polymeric mineral surface active agent separated from the fluoride or other incompatible component. Another option is to formulate non-aqueous, essentially non-aqueous or limited water compositions to minimize reaction between the PMSA and other components.

A preferred PMSA is a polyphosphate. A polyphosphate is generally understood to consist of two or more phosphate molecules arranged primarily in a linear configuration, although some cyclic derivatives may be present. Although pyrophosphates (n=2) are technically polyphosphates, the polyphosphates desired are those having around three or more phosphate groups so that surface adsorption at effective concentrations produces sufficient non-bound phosphate functions, which enhance the anionic surface charge as well as hydrophilic character of the surfaces. The inorganic polyphosphate salts desired include tripolyphosphate, tetrapolyphosphate and hexametaphosphate, among others. Polyphosphates larger than tetrapolyphosphate usually occur as amorphous glassy materials. Preferred in this invention are the linear polyphosphates having the formula:

wherein X is sodium, potassium or ammonium and n averages from about 3 to about 125. Preferred polyphosphates are those having n averaging from about 6 to about 21, such as those commercially known as Sodaphos (n≈6), Hexaphos (n≈13), and Glass H (n≈21) and manufactured by FMC Corporation and Astaris. These polyphosphates may be used alone or in combination. Polyphosphates are susceptible to hydrolysis in high water formulations at acid pH, particularly below pH 5. Thus it is preferred to use longer-chain polyphosphates, in particular Glass H with an average chain length of about 21. It is believed such longer-chain polyphosphates when undergoing hydrolysis produce shorter-chain polyphosphates which are still effective to deposit onto teeth and provide a stain preventive benefit.

Other polyphosphorylated compounds may be used in addition to or instead of the polyphosphate, in particular polyphosphorylated inositol compounds such as phytic acid, myo-inositol pentakis(dihydrogen phosphate); myo-inositol tetrakis(dihydrogen phosphate), myo-inositol trikis(dihydrogen phosphate), and an alkali metal, alkaline earth metal or ammonium salt thereof. Preferred herein is phytic acid, also known as myo-inositol 1,2,3,4,5,6-hexakis (dihydrogen phosphate) or inositol hexaphosphoric acid, and its alkali metal, alkaline earth metal or ammonium salts. Herein, the term "phytate" includes phytic acid and its salts as well as the other polyphosphorylated inositol compounds.

The amount of tooth substantive agent will typically be from about 0.1% to about 35% by weight of the total oral composition. In dentifrice formulations, the amount is preferably from about 2% to about 30%, more preferably from about 5% to about 25%, and most preferably from about 6% to about 20%. In mouthrinse compositions, the amount of tooth substantive agent is preferably from about 0.1% to 5% and more preferably from about 0.5% to about 3%.

In addition to creating the surface modifying effects, the tooth substantive agent may also function to solubilize insoluble salts. For example, Glass H polyphosphate has been found to solubilize insoluble stannous salts. Thus, in compositions containing stannous salts, Glass H contributes to decreasing the stain promoting effect of stannous.

5. Additional Orally Acceptable Carriers

The present compositions may also comprise surfactants, also commonly referred to as sudsing agents. Suitable surfactants are those that are reasonably stable and foam throughout a wide pH range. The surfactant may be anionic, nonionic, amphoteric, zwitterionic, cationic, or mixtures thereof. Anionic surfactants useful herein include the water-soluble salts of alkyl sulfates having from 8 to 20 carbon atoms in the alkyl radical (e.g., sodium alkyl sulfate) and the water-soluble salts of sulfonated monoglycerides of fatty acids having from 8 to 20 carbon atoms. Sodium lauryl sulfate and sodium coconut monoglyceride sulfonates are examples of anionic surfactants of this type. Other suitable anionic surfactants are sarcosinates, such as sodium lauroyl sarcosinate, taurates, sodium lauryl sulfoacetate, sodium lauroyl isethionate, sodium laureth carboxylate, and sodium dodecyl benzenesulfonate. Mixtures of anionic surfactants can also be employed. Many suitable anionic surfactants are disclosed by Agricola et al., U.S. Pat. No. 3,959,458, issued May 25, 1976. Nonionic surfactants which can be used in the compositions of the present invention can be broadly defined as compounds produced by the condensation of alkylene oxide groups (hydrophilic in nature) with an organic hydrophobic compound which may be aliphatic or alkyl-aromatic in nature. Examples of suitable nonionic surfactants include poloxamers (sold under trade names Pluronic and Pluraflo), polyoxyethylene, polyoxyethylene sorbitan esters (sold under trade name Tweens), Polyoxyl 40 hydrogenated castor oil, fatty alcohol ethoxylates, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides, and mixtures of such materials. The amphoteric surfactants useful in the present invention can be broadly described as derivatives of aliphatic secondary and tertiary amines in which the aliphatic radical can be a straight chain or branched and wherein one of the aliphatic substituents contains from about 8 to about 18 carbon atoms and one contains an anionic water-solubilizing group, e.g., carboxylate, sulfonate, sulfate, phosphate, or phosphonate. Other suitable amphoteric surfactants are betaines, specifically cocamidopropyl betaine. Mixtures of amphoteric surfactants can also be employed. Many of these suitable nonionic and amphoteric surfactants are disclosed by Gieske et al., U.S. Pat. No. 4,051,234, issued Sep. 27, 1977. The present composition typically comprises one or more surfactants each at a level of from about 0.25% to about 12%, preferably from about 0.5% to about 8%, and most preferably from about 1% to about 6%, by weight.

Poloxamers are among the preferred surfactants employed in the present compositions. A poloxamer may also function as an emulsifying agent, binder, stabilizer, and other related functions. Suitable poloxamers for this invention are Poloxamer 407 and Pluraflo L4370.

Other emulsifying agents that may be used in the present compositions include polymeric emulsifiers such as the Pemulen® series available from B.F. Goodrich, and which are predominantly high molecular weight polyacrylic acid polymers useful as emulsifiers for hydrophobic substances.

The present invention may also include an alkali metal bicarbonate salt, which may serve a number of functions including abrasive, deodorant, buffering and adjusting pH. Sodium bicarbonate, also, known as baking soda, is a commonly used alkali metal bicarbonate salt. The present composition may contain from about 0.5% to about 30%, preferably from about 0.5% to about 15%, and most preferably from about 0.5% to about 5% of an alkali metal bicarbonate salt.

Titanium dioxide may also be added to the present composition. Titanium dioxide is a white powder which adds opacity to the compositions. Titanium dioxide generally comprises from about 0.25% to about 5% by weight of dentifrice compositions.

Coloring agents may also be added to the present composition. The coloring agent may be in the form of an aqueous solution, preferably 1% coloring agent in a solution of water. Color solutions generally comprise from about 0.01% to about 5%, by weight of the composition.

Other optional agents that may be used in the present compositions include dimethicone copolyols selected from alkyl- and alkoxy-dimethicone copolyols, such as C12 to C20 alkyl dimethicone copolyols and mixtures thereof. Highly preferred is cetyl dimethicone copolyol marketed under the trade name Abil EM90. The dimethicone copolyol is generally present at a level of from about 0.01% to about 25%, preferably from about 0.1% to about 5%, more preferably from about 0.5% to about 1.5% by weight. The dimethicone copolyols aid in providing positive tooth feel benefits.

Method of Use

The present invention also relates to methods for cleaning teeth and preventing undesirable oral cavity conditions including caries, microbial infection, plaque, calculus, stain and oral malodor and dental erosion.

The method of use herein comprises contacting a subject's dental enamel surfaces and oral mucosa with the oral compositions according to the present invention. The method of use may be by brushing with a dentifrice, rinsing with a dentifrice slurry or mouthrinse, or chewing a gum product. Other methods include contacting the topical oral gel, mouthspray, or other form with the subject's teeth and oral mucosa. The subject may be any person or animal whose tooth surface is contacted with the oral composition. By animal is meant to include household pets or other domestic animals, or animals kept in captivity.

For example, a method of treatment may include a person brushing a dog's teeth with one of the dentifrice compositions. Another example would include the rinsing of a cat's mouth with an oral composition for a sufficient amount of time to see a benefit. Pet care products such as chews and toys may be formulated to contain the present oral compositions. The composition is incorporated into a relatively supple but strong and durable material such as rawhide, ropes made from natural or synthetic fibers, and polymeric articles made from nylon, polyester or thermoplastic polyurethane. As the animal chews, licks or gnaws the product, the incorporated active elements are released into the animal's oral cavity into a salivary medium, comparable to an effective brushing or rinsing.

EXAMPLES

The following examples further describe and demonstrate embodiments within the scope of the present invention. These examples are given solely for the purpose of illustration and are not to be construed as limitations of the present invention as many variations thereof are possible without departing from the spirit and scope.

Flavor systems containing a mint oil and protectant component are described below.

Example I

| Ingredient | Wt. % |
|---|---|
| Corn mint | 40% |
| Anethole | 15% |
| Menthol | 10% |
| Peppermint | 30% |
| Cinnamaldehyde | 5% |

Example II

| Ingredient | Wt % |
|---|---|
| WS-3 coolant | 10% |
| Spearmint oil | 15% |
| Peppermint oil | 30% |

-continued

| Ingredient | Wt % |
|---|---|
| Anethole | 4% |
| Menthol | 24% |
| Ethyl vanillin | 7% |
| Heliotropine | 3% |
| Vanillin | 7% |

Oral compositions containing stannous ions, a flavor system containing mint oils and protectant(s) as in Example I and II, and orally acceptable carriers are described below. Oral compositions containing stannous and a flavor system comprising a mint oil with a protectant will not have an off odor and flavor. Oral compositions containing the same amount of stannous and mint oil but not containing a protectant will have a noticeable malodor and off taste making the oral composition not aesthetically pleasing.

Example III

| Ingredient | IIIA | IIIB | IIIC | IIID | IIIE | IIIF | IIIG |
|---|---|---|---|---|---|---|---|
| Phytic Acid (20% Soln) | 4.000 | 2.000 | | | 10.000 | | |
| Na Phytate (20% Soln.) | | | 10.000 | 4.000 | | | |
| Zn Carbonate[1] | 2.000 | 1.000 | | 2.000 | | | |
| Zn Oxide | | | 5.000 | | | | |
| Zn Pyrophosphate | | | | | 8.000 | | |
| Zn Lactate | | | | | | 2.500 | |
| Na Polyphosphate | | | | | | 13.000 | |
| Stannous Fluoride | 0.454 | 0.454 | | 0.454 | | 0.454 | 0.454 |
| Sodium Fluoride | | | 0.243 | | 0.243 | | |
| Stannous Chloride | | | 1.500 | | 1.000 | | 1.500 |
| Tea Extract | | | | 2.000 | | | |
| EGCG | | | | | | 1.000 | 1.000 |
| Sodium Gluconate | 0.672 | 0.600 | 0.672 | 0.600 | 0.672 | 0.652 | 2.100 |
| Sorbitol Soln | 34.275 | 35.785 | 34.275 | 35.785 | 34.275 | | 37.496 |
| Glycerin | | | | | | 38.519 | 14.425 |
| HEC | 0.300 | 0.300 | 0.300 | 0.300 | 0.300 | | |
| Na CMC | 1.200 | 1.300 | 1.200 | 1.300 | 1.200 | | 0.600 |
| Carrageenan | 0.500 | 0.500 | 0.500 | 0.500 | 0.500 | 0.600 | |
| Xanthan Gum | | | | | | 0.350 | 0.700 |
| PEG | | | | | | 7.000 | |
| Propylene Glycol | | | | | | 7.000 | |
| Silica Abrasive | 20.000 | 16.000 | 20.000 | 16.000 | 20.000 | 25.000 | 20.000 |
| TiO$_2$ (Anatase) | 0.525 | 0.525 | 0.525 | 0.525 | 0.525 | | 0.525 |
| SLS (28% Soln.) | 4.000 | 7.500 | 4.000 | 7.500 | 4.000 | 2.500 | 5.000 |
| Na Saccharin | 0.250 | 0.250 | 0.250 | 0.250 | 0.250 | 0.500 | 0.300 |
| Flavor | 0.950 | 0.950 | 0.950 | 0.950 | 0.950 | 0.800 | 1.000 |
| NaOH | 0.006 | 0.122 | 0.006 | 0.122 | 0.006 | | 0.600 |
| Na Phosphate Tribasic | | | | | | 1.100 | |
| Water and Minors, e.g., | QS | QS | QS | QS | QS | QS | QS |

[1]Zinc Carbonate AC supplied by Bruggemann Chemical: Newtown Square, PA, USA

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An oral care composition comprising:
   a. stannous ions in an amount of about 1000 ppm or greater than 1000 ppm;
   b. a flavor system to provide a mint-dominant flavor comprising (i) a mint oil which has been found to contain dimethyl sulfoxide (DMSO) at levels sufficient to react with stannous ions to form mercaptans and dimethyl sulfide that cause malodor and (ii) a protectant component selected from copper salts, ascorbic acid, cis-jasmone, 2,5-dimethyl-4-hydroxy-3(2H)-furanone, 5-ethyl-3-hydroxy-4-methyl-2(5H)-furanone, anisaldehyde, 3,4-methylenedioxybenzaldehyde, 3,4-dimethoxybenzaldehyde, 4-hydroxybenzaldehyde, 2-methoxybenzaldehyde, benzaldehyde, cinnamaldehyde; hexyl cinnamaldehyde, α-methyl cinnamaldehyde, ortho-methoxy cinnamaldehyde, α-amyl cinnamaldehyde and mixtures thereof; and
   c. orally acceptable carriers;

wherein the ratio of protectant component to mint oil is from about 1:1 to about 1:200 by weight when the protectant is other than the cinnamaldehyde compounds and from about 1:2 to about 1:16 by weight when the protectant is any of the cinnamaldehyde compounds, sufficient to reduce the level of mercaptans and dimethyl sulfide and malodor therefrom.

2. The oral composition according to claim 1 wherein the mint oil is selected from peppermint, spearmint, corn mint and mixtures thereof.

3. The oral composition of claim 1 wherein the oral composition is in a form selected from a dentifrice, tooth gel, subgingival gel, mouthrinse, mouthspray, mousse, foam, denture care product, lozenge, chewable tablet, chewing gum and strip for direct attachment to teeth.

4. The oral composition of claim 1 wherein the stannous ions are from one or a mixture of stannous salts selected from stannous fluoride, stannous chloride, stannous chloride dihydrate, stannous acetate, stannous gluconate, stannous oxalate, stannous sulfate, stannous lactate, and stannous tartrate.

5. The oral composition of claim 1 wherein the flavor system is from about 0.01 to about 5% by weight.

6. The oral composition of claim 1 comprising one or more additional flavor ingredients selected from oil of wintergreen, clove bud oil, cassia, sage, parsley oil, marjoram, lemon, orange, propenyl guaethol, heliotropine, 4-cis-heptenal, diacetyl, methyl-ρ-tert-butyl phenyl acetate, menthol, methyl salicylate, ethyl salicylate, 1-menthyl acetate, oxanone, α-irisone, methyl cinnamate, ethyl cinnamate, butyl cinnamate, ethyl butyrate, ethyl acetate, methyl anthranilate, iso-amyl acetate, iso-amyl butyrate, allyl caproate, eugenol, eucalyptol, thymol, cinnamic alcohol, octanol, octanal, decanol, decanal, phenylethyl alcohol, benzyl alcohol, α-terpineol, linalool, limonene, citral, maltol, ethyl maltol, anethole, dihydroanethole, carvone, menthone, β-damascenone, ionone, γ-decalactone, γ-nonalactone, γ-undecalactone, and mixtures thereof.

7. The oral composition of claim 1 additionally comprising an ingredient selected from the group consisting of a polyphosphate, phytate, EDTA, and combinations thereof.

* * * * *